United States Patent
Tsuruta (10) Patent No.: US 7,282,055 B2
(45) Date of Patent: Oct. 16, 2007

(54) MEDICAL RETRIEVAL INSTRUMENT

(75) Inventor: Minoru Tsuruta, Hino (JP)

(73) Assignee: Olympus Corporation, Tokyo (JP)

( * ) Notice: Subject to any disclaimer, the term of this patent is extended or adjusted under 35 U.S.C. 154(b) by 130 days.

(21) Appl. No.: 10/084,557

(22) Filed: Feb. 26, 2002

(65) Prior Publication Data
US 2002/0133170 A1     Sep. 19, 2002

(30) Foreign Application Priority Data
Mar. 13, 2001   (JP) ............................. 2001-070954

(51) Int. Cl.
*A61B 17/22* (2006.01)
(52) U.S. Cl. ................. 606/127; 606/128; 606/170; 606/171
(58) Field of Classification Search ................. 606/127, 606/128, 200
See application file for complete search history.

(56) References Cited

U.S. PATENT DOCUMENTS

| 5,064,428 | A | * | 11/1991 | Cope et al. ................. 606/127 |
| 5,190,555 | A | * | 3/1993 | Wetter et al. ................. 606/114 |
| 5,190,557 | A | * | 3/1993 | Borodulin et al. .......... 606/127 |
| 5,403,324 | A | * | 4/1995 | Ciervo et al. ................. 606/128 |
| 5,496,330 | A | * | 3/1996 | Bates et al. ................. 606/127 |
| 5,792,145 | A | | 8/1998 | Bates et al. |
| 5,906,622 | A | * | 5/1999 | Lippitt et al. ................. 606/127 |
| 6,123,665 | A | * | 9/2000 | Kawano ....................... 600/104 |
| 6,174,318 | B1 | | 1/2001 | Bates et al. |
| 6,264,664 | B1 | * | 7/2001 | Avellanet ..................... 606/128 |

FOREIGN PATENT DOCUMENTS

| DE | 33 13 895 A1 | | 10/1984 |
| JP | 172813 | * | 5/1989 |
| JP | 1-72813 | | 12/1989 |

* cited by examiner

*Primary Examiner*—Anhtuan T. Nguyen
*Assistant Examiner*—Charles Sam
(74) *Attorney, Agent, or Firm*—Scully, Scott, Murphy & Presser, P.C.

(57) ABSTRACT

A medical retrieval instrument of the present invention includes a plurality of filaments for holding an object and a hollow section through which a first end of each of said plurality of filaments passes. The hollow section comprises a plurality of fixing sections for fixing a second end of each of said plurality of filaments, for example. The hollow section is arranged in a distal end portion of a sheath. The hollow section is inserted into the body cavity by the sheath and then holds an object such as renal calculus or ureteral calculus in the body cavity and retrieves them to outside the body.

6 Claims, 6 Drawing Sheets

MEDICAL RETRIEVAL INSTRUMENT

CROSS REFERENCE TO RELATED APPLICATION

This application is based on and claims priority of Japanese Patent Application No. 2001-70954 filed on Mar. 13, 2001, the contents of which are incorporated herein by reference.

BACKGROUND OF THE INVENTION

1. Field of the Invention

The present invention relates to a medical retrieval instrument.

2. Description of the Related Art

Generally, in a medical retrieval instrument with a wire basket, forward and backward movement of an operation wire inserted into a sheath causes the wire basket mounted near the distal end of the sheath to open and close relative to the distal end of the sheath. The wire basket holds such objects as nephrolith or ureterolith or the like from a body cavity and then retrieves the object for inspection outside the body.

Japanese Utility Model Laid-Open Publication No.1-172813 discloses a medical retrieval instrument in which one end of a wire basket is connected to the distal end of an operation wire, whereas the other end of the wire basket is connected to the distal end of a sheath.

However, the medical retrieval instrument of this Japanese Utility Model Laid-Open Publication No.1-172813 has a problem. Unless one end of the wire basket is fixed to the distal end of the sheath precisely at a predetermined position and in a predetermined direction, the wire basket does not expand to a desired shape. As a result, a stone captured in the wire basket cannot be held efficiently.

Regardless of the above-mentioned problem, a medical retrieval instrument of the Japanese Utility Model Laid-Open Publication No.1-172813 has a wire basket, one end of which is only held by a ring-like holding tube and fixed to a sheath. Such a mounting configuration is unstable, since one end portion of the wire basket easily slips on the outer surface. Therefore, it takes more time to mount one end portion of the wire basket at a predetermined position and in a predetermined direction.

BRIEF SUMMARY OF THE INVENTION

The present invention provides a medical retrieval instrument which overcomes the problems associated with the prior art.

Accordingly, a medical retrieval instrument is provided. The medical retrieval instrument comprises a plurality of filaments for holding an object, and a hollow section, through which a first end of each of the plurality of filaments passes, the hollow section including a fixing section for fixing a second end of each of the plurality of filaments.

Also provided is a medical retrieval instrument comprising a plurality of filaments for holding an object, and a tube, through which a first end portion of each of the plurality of filaments passes, the tube including holes for fixing a second end portion of each of the plurality of filaments.

Still also provided is a medical retrieval instrument comprising a plurality of filaments for holding an object, a first tube including a plurality of grooves in which a first end portion of each of the plurality of filaments is disposed, the plurality of grooves are formed on one of an external or internal surface of the first tube; and a second tube engaged with the first tube for fixing the first end portion of each of the plurality of filaments disposed in the plurality of grooves.

BRIEF DESCRIPTION OF THE DRAWINGS

The accompanying drawings, which are incorporated in and constitute a part of the specification, illustrate exemplary embodiments of the invention, and together with the general description above and the detailed description of illustrative embodiments given below, serve to explain the principles of the invention.

DETAILED DESCRIPTION

With reference to FIGS. 1-4, a first embodiment of medical instrument according to the present invention will now be explained.

The medical instrument is a medical retrieval instrument for retrieving an object such as a stone or the like from a body cavity. The medical retrieval instrument is preferably used with an endoscope (not shown). If this medical retrieval instrument is used with an endoscope, the medical retrieval instrument is inserted into a channel in an insertion section of an endoscope inserted into the body cavity. The channel is a tunnel extending from the proximal end to the distal end in the insertion section. The medical retrieval instrument extrudes out of the distal end of the insertion section and is provided at a predetermined position in the view of the endoscope. Later, the medical retrieval instrument is used at a located position for desired medical treatment. This medical retrieval instrument can be used in all the embodiments mentioned below.

Figure 1A:
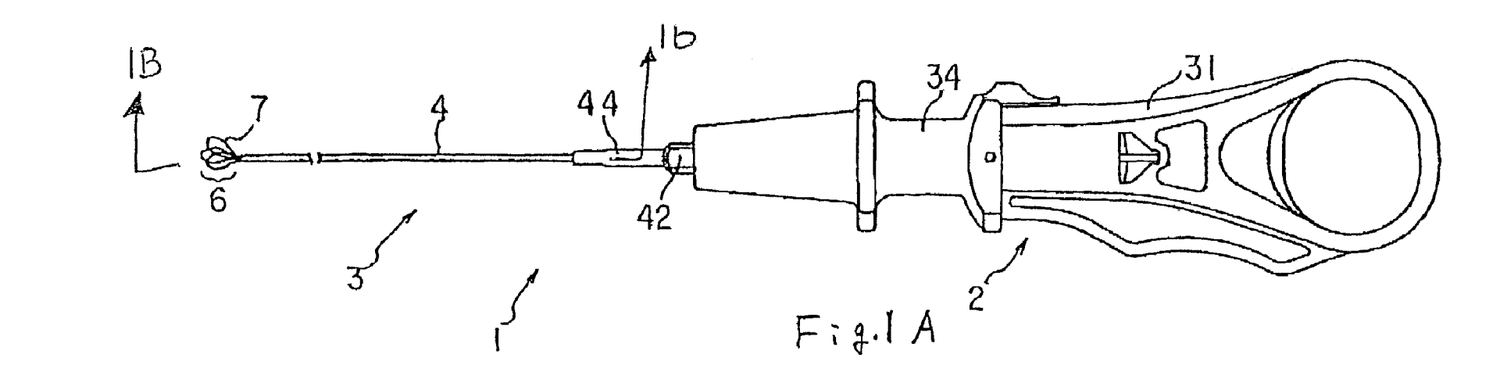
FIG. 1A illustrates a side view schematically illustrating a medical retrieval instrument according to a first embodiment of the present invention.

A medical retrieval instrument 1 according to the first embodiment comprises an operation section 2 and an insertion section 3, as shown in FIG. 1A. The insertion section 3 is not to be confused with the above described insertion section of the endoscope. The insertion section 3 includes a sheath 4, which is to be inserted into the body cavity of a patient, preferably through the endoscope channel (not shown). The sheath 4 is preferably formed in a tubular shape and made of a flexible material such as fluorocarbon resin of FEP, PTFE, PFA, ETFE, polyimide or the like. Alternatively, the sheath 4, can be fabricated of a substantially rigid material, such as stainless steel, a rigid plastic, a rigid synthetic resin, or the like.

Into the above-mentioned sheath 4, an operation wire 5 is inserted as an operation member which is moved forward and backward by manipulation of the operation section 2. A holding section 6, formed as a basket is mounted to the distal end of the sheath 4. The holding section 6 is formed of a plurality of holding filaments 7 (a plurality is used herein to mean two or more). Each holding filament 7 extends like a loop, unless the holding filament 7 holds an object. The holding filament 7 is elastic, so that its shape is changeable. These filaments 7 form a basket portion for holding an object.

Figure 1B:
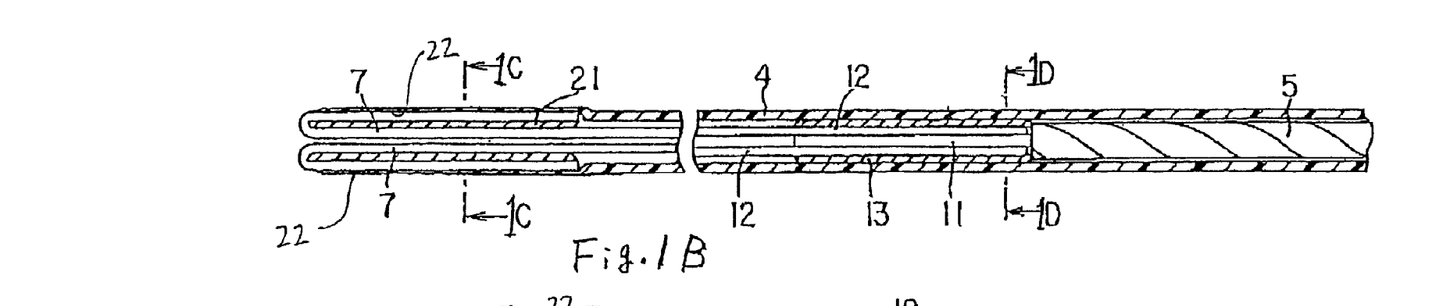
FIG. 1B illustrates a vertical sectional view taken along line 1B-1B on FIG. 1A.

The holding filament 7 is formed by filaments of the operation wire 5 as shown in FIG. 1B. A plurality of filaments 12 are wound around the core line 11, to form the operation wire 5. In the holding section 6 of the first embodiment, the distal end portion of the core line 11 of the operation wire 5 is removed. The filaments 12 remaining on the distal end portion of the core line 11 are used as the holding filaments 7. The holding filaments 7 may also be formed of another member attached to the operation wire 5, without the filament 12 of the operation wire 5. In this case, the operation wire 5 is made of such material as stainless steel, which easily transmits its operating force.

A plurality of holding filaments 7 (the holding section is shown by way of example having three filaments 7) form the above-mentioned holding section 6. In the holding section 6, one end of each holding filament 7 is fixedly connected to the end of the operation wire 5, and the other end of each holding filament 7 is fixedly connected to the distal end of sheath 4. Each holding filament 7 protrudes out and retracts in the end opening of the sheath 4, by the forward and backward movement of the operation wire 5.

Figure 2:
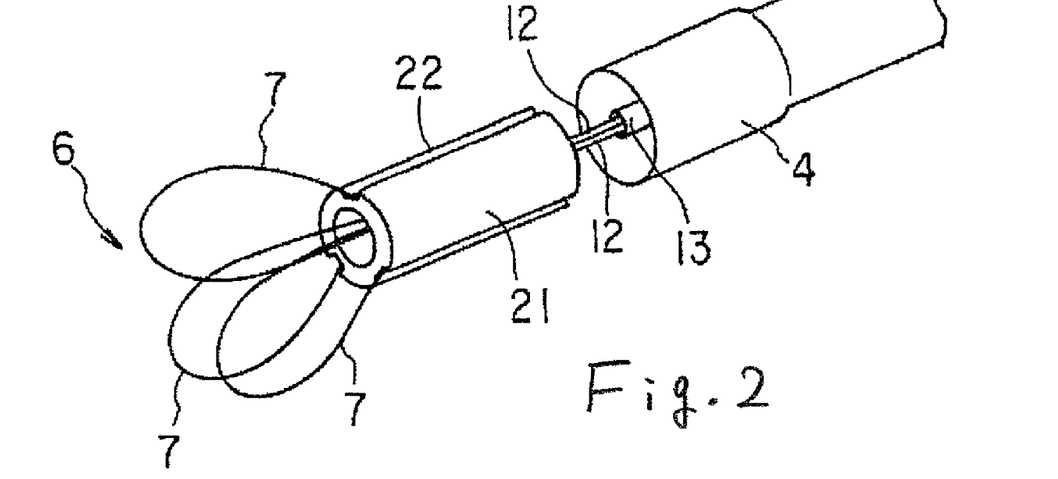
FIG. 2 illustrates an expanded perspective view of a holding section of the medical retrieval instrument of FIG. 1A.

As shown in FIG. 1A and FIG. 2, the loop portion of each holding filament 7 protrudes from the end opening of the sheath 4. As a result, holding filaments 7 are equally spaced and radiate, extending like a loop so that a basket holding section is formed.

Figure 1C:
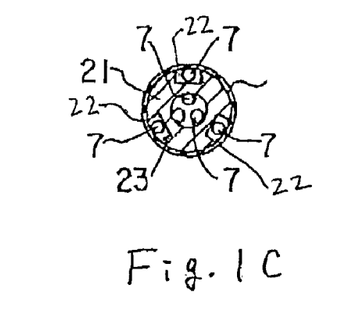
FIG. 1C illustrates a transverse sectional view taken along the line 1C-1C in FIG. 1B.
Figure 1D:
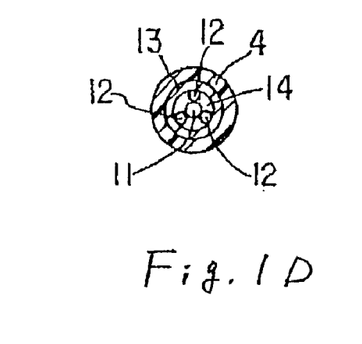
FIG. 1D illustrates a transverse sectional view taken along the line 1D-1D in FIG. 1B.

A fixing pipe 13 connects the proximal end portion of the filament 12 forming each holding filament 7 to the core line 11 which is the distal end portion of the operation wire 5. Moreover, an adhesive 14 fixes the proximal end portion of the filament 12, and the operation wire 5 fixes to the fixing pipe 13. As shown in FIGS. 1B-D, each filament 12 parallels the longitudinal direction of the sheath 4. Each filament 12 also extends straightforward from the operation wire 5 towards the distal end of the sheath 4.

The distal end of each filament 12 is used as the holding filament 7. The holding filament 7 protrudes from the distal end of the sheath 4 through a fixing member 21 being a pipe which is engaged into and fixed to the distal end portion of sheath 4. A positioning and regulating means including the fixing member 21, fixedly connects the distal end portion of each holding filament 7 to a predetermined position on the distal end of the sheath 4.

The positioning and regulating means is constituted as follows, so that the distal end of each holding filament 7 is positioned at the distal end portion of the sheath 4. As shown in FIG. 2, a plurality of grooves 22 are formed on the outer surface of the fixing member 21 and throughout the fixing member 21. The grooves 22 extend parallel to the extending direction of the filaments 12. The number of grooves 22 can be varied, according to the number of holding filaments 7. For example, the positioning and regulating means shown in FIG. 1C has three grooves 22. Each groove 22 is located in the isometric interval. The grooves 22 are positioned according to a position at which one holding filament 7 should be fixed to the fixing member 21.

As shown in FIG. 1C, an end portion of each holding filament 7 is engaged into one groove 22 of the fixing member 21. Therefore, the end of each holding filament 7 is located at a position. The direction of the holding filament 7 is thereby determined. An adhesive 23 filled in the groove 22 fixes the holding filament 7. The adhesive 23 is tightly embedded in the groove 22. Each groove 22 is covered with the inner surface of the end portion of sheath 4. The fixing member 21 (a first member) engages with the distal end portion of sheath 4 (a second member). The holding filament 7 is held between the groove 22 as a positioning section and the distal end portion of sheath 4 as a holding section. The positioning section and the holding section form a fixing section for fixing the holding filament 7. The fixing member 21 is preferably a tube so that the holding filament 7 can be inserted into the inside thereof. In this embodiment, each groove 22 extends out almost in the same direction as the end portion of sheath 4 or the fixing member 21 does.

The holding filament 7 is preferably formed of polyethylene terephthalate, polybutylene terephthalate, polyimide, or the like, which is a resin having some degree of elasticity and difficult to be kept bent, or NiTi alloy or the like. The diameter of holding filament 7 is preferably between 0.14 and 0.2 mm. The holding filament 7 is preferably a flexible filament resin or a filament material. The outer diameter of sheath 4 is usually set to be 1-2 mm.

The more preferable the width of the groove 22 and the outer diameter of holding filament 7 are, the more tightly the holding filament 7 is engaged in the groove 22. However, if the holding filament 7 can be located at a certain position, the width of the groove 22 may be larger than the outer diameter of the holding filament 7. For example, the width of the groove 22 may be larger than the outer diameter of holding filament 7, if the holding filament 7 is pressed between the inner surface of the sheath 4 and the bottom portion of the groove 22. Moreover, the holding filament 7 can be prevented from twisting, if the groove 22, in which the holding filament 7 is engaged, extends longer. Therefore, if the length of groove 22 is long enough with respect to the width of groove 22, the width of groove 22 can be larger than the outer diameter of holding filament 7.

By such positioning means, a plurality of filaments 7 forming the holding section 6 are arranged at a predetermined position and in a predetermined direction.

Figure 4A:
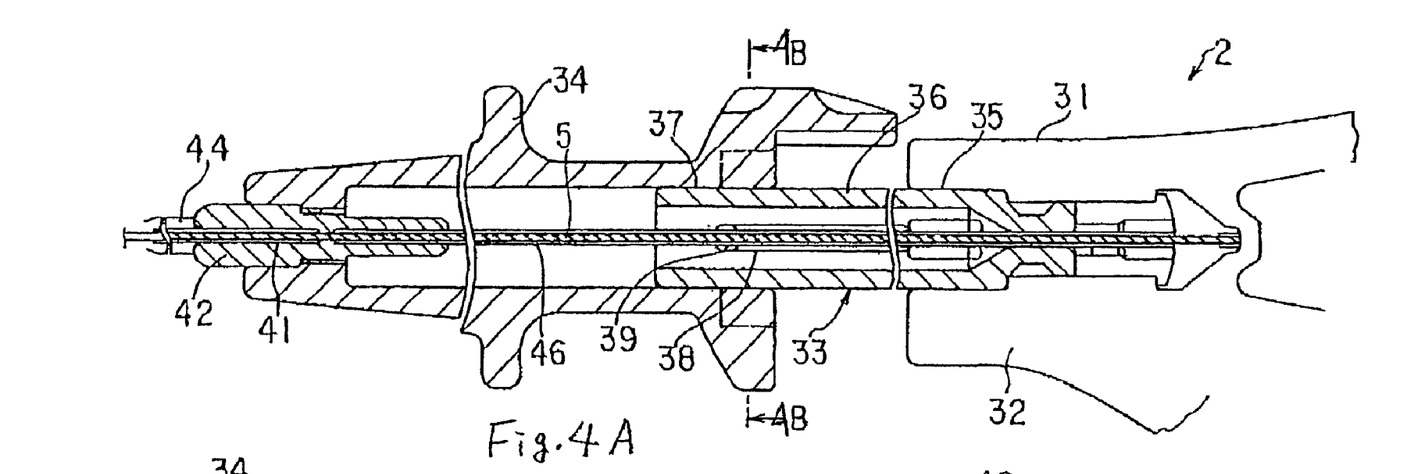
FIG. 4A illustrates a vertical section of an operation section of the medical retrieval instrument of FIG. 1A.

The following explanation relates to the above-mentioned operation section 2. The operation section 2 comprises the main body 31 of the operation section 2. As shown in FIG. 4A, a gripping member 32 and a tubular guiding member 33 are combined so as to form the main body 31. A slider 34 is slidably attached to the guiding member 33. The front end portion of gripping member 32 comprises an insert hole 35 into which the rear end portion of the guiding member 33 is engaged. The insert hole 35 has a structure by which the gripping member 32 and the guiding member 33 do not rotate around the axial direction of the insertion section 3.

The front-end portion of the above-mentioned guiding member 33 comprises a tubular guiding section 36. The above-mentioned slider 34 is engaged, to the outer surface of the guiding section 36 such that the slider 34 can be slid in the forward and backward (distal and proximal) directions.

Figure 4B:
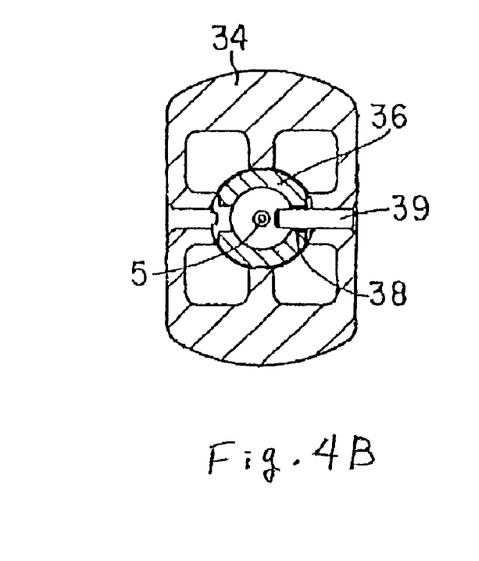
FIG. 4B illustrates a transverse sectional view taken along the line 4B-4B in FIG. 4A.

FIG. 4B shows that the peripheral portion of guiding section 36 and a guide hole 37 of the slider 34 engaged therewith have a round shape in cross-section. Therefore, the following rotation control means is provided, so that these do not rotate around the axial direction of the insertion section.

As shown in FIG. 4B, a wall portion the guiding section 36 of the above-mentioned guiding member 33 has a long slit 38 longitudinally. A stopper pin 39 fixed to the sidewall portion of the above-mentioned slider 34 is slidably engaged into the slit 38. The stopper pin 39 controls the above-mentioned slider 34 and the main body 31 of the operation section, so that they do not rotate. The axial movement ranges of the above-mentioned slider 34 and the main body 31 of the operation section are limited, since the movement range of the stopper pin 39 is determined according to the length of the slit 38. Additionally, the engagement of the stopper pin 39 with the slit 38 limits the relative rotation of the above-mentioned slider 34 and the main body 31.

A connecting member 42 is provided to the front-end wall of the above-mentioned slider 34. The connecting member 42 comprises a through hole 41 coaxial with the guide hole 37 of the above-mentioned guiding member 33. The proximal end portion of the sheath 4 is engaged into the through hole 41 via a pipe 43. The sheath 4 is fixedly connected to the connecting member 42. The pipe 43 extends forward out of the through hole 41 of the connecting member 42. Also, the extending end of the pipe 43 is engaged with the proximal end portion of a covering tube 44 described later.

Figures 4C, 4D:
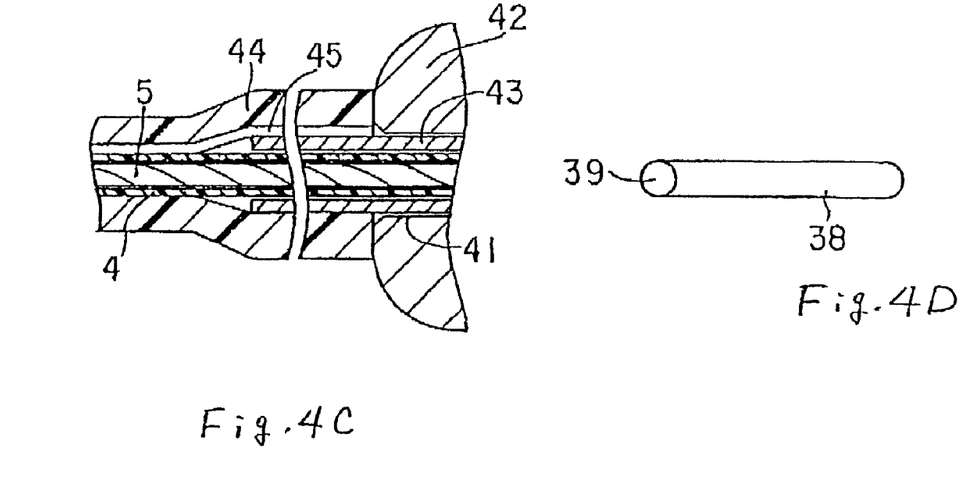
FIG. 4C illustrates a vertical section of a connection portion covered with a covering tube at a proximal portion of a sheath.
FIG. 4D illustrates an explanatory view showing the range in which a slit and a stopper pin move.

As shown in FIG. 4C, the proximal periphery of sheath 4 is covered with the flexible covering tube 44. An elastic member 45 is provided inside the covering tube 44 so as to strengthen the covering tube 44. The covering tube 44 covers the end portion of pipe 43 protruding out of the forward end of the connecting member 42, over the outer surface of the proximal portion of sheath 4.

The operation wire 5 guided by the sheath 4 is led into the above-mentioned slider 34 and fixed to the gripping member 32 through the guiding member 33 of the main body 31. The operation wire 5 is engaged with a pipe 46, so that the operation wire 5 is prevented from deflecting in the slider 34 and the guiding member 33.

The following explanation relates to the use of the medical retrieval instrument 1 with an endoscope. When an operator inserts the insertion section 3 of the medical retrieval instrument 1 into a channel of an endoscope, the operator moves the main body 31 toward the proximal side and pulls the operation wire 5, against the slider 34. As a result, the holding filament 7 of the holding section 6 is shown drawn into the sheath 4. In FIG. 1B, the holding filament 7 of the holding section 6 is drawn into the sheath 4. As shown in FIG. 1B, each holding filament 7 of the holding section 6 is accommodated inside the sheath 4, not extending outward from the outer diameter of the sheath 4. When the insertion section 3 of the medical retrieval instrument 1 is inserted into the channel of an endoscope, therefore, the inner surface of the channel does not interfere with the holding filaments 7 of the holding section 6.

Figure 3:
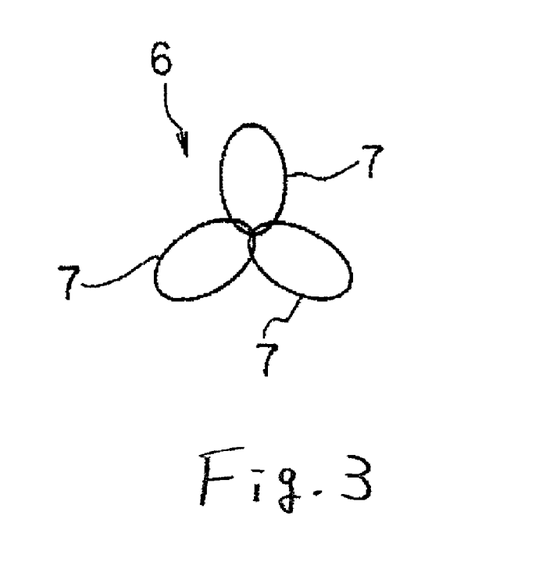
FIG. 3 illustrates a front view of a holding section of the medical retrieval instrument of FIG. 2.

After the distal end of the insertion section 3 of the medical retrieval instrument 1 is guided into the body cavity, the above-mentioned holding section 6 protrudes from the end of sheath 4, as the operator pulls and pushes the above-mentioned operation wire 5 by operation of the slider 34 relative to the main body 31. As shown in FIGS. 1A and 3, the protrusion of the holding section 6 leads each holding filament 7 to equally expand like a loop and to radiate.

After the operator moves this expanded holding section 6 close to a stone (or other object) to be retrieved, the stone is captured inside the holding section 6. Unless the stone is captured in the holding section 6, the holding section 6 opens and closes repeatedly. As a result of the opening and closing of the holding section 6, the stone is captured in the holding section 6.

After the operator captures the stone in the holding section 6, he either withdraws only the medical retrieval instrument 1 from the endoscope channel or he withdraws the endoscope itself out of the body, and collects the stone.

In the first embodiment, an end portion of each holding filament 7 forming the holding section 6 is engaged into a corresponding groove 22 of the fixing member 21. The groove 22 positions an end portion of each holding filament 7 and correctly regulates the direction in which the holding filament 7 extends out. In the assembly, if only one end portion of the holding filament 7 is engaged into the corresponding groove 22, positioning is finished. Since one end portion of each filament is fixed at a predetermined position and in a predetermined direction, assembly is easily done.

The first embodiment makes assembly easier than the medical retrieval instruments of the prior art. Also, a plurality of filaments 7 forming the holding section 6 are correctly arranged at a predetermined position and in a predetermined direction. Even a bending holding filament 7 may be mounted, at a predetermined position and in a predetermined direction where the shape of the holding filament 7 can be made stable.

Figure 5A:
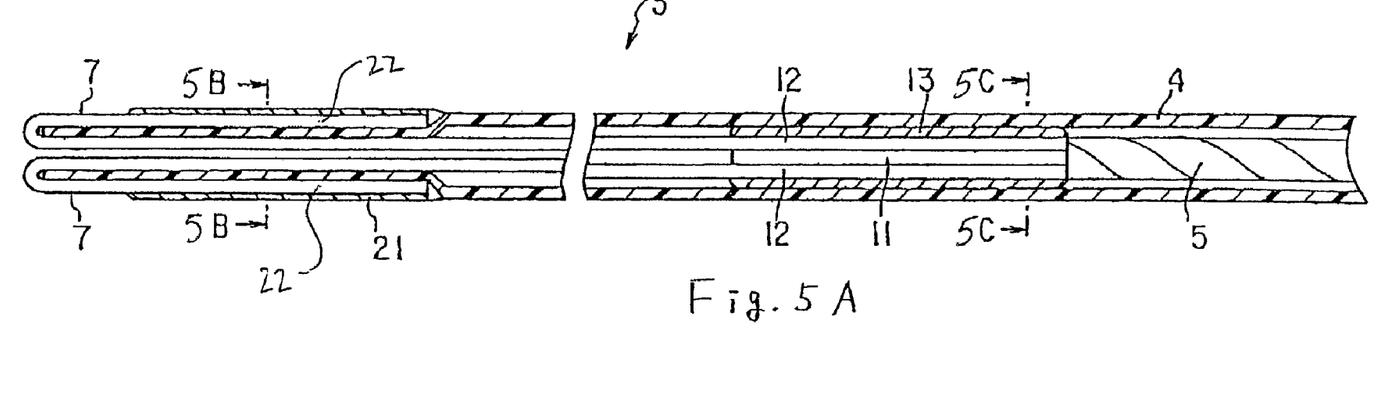
FIG. 5A illustrates a vertical section showing the vicinity of the distal end portion of an insertion section in a medical retrieval instrument according to a second embodiment of the present invention.
Figure 5B:
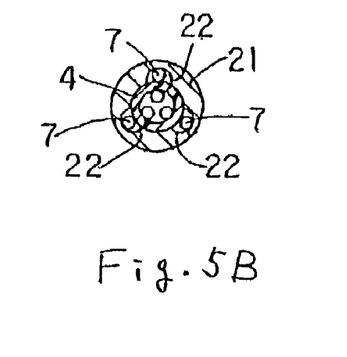
FIG. 5B illustrates a transverse sectional view taken along the line 5B-5B in FIG. 5A.
Figure 5C:
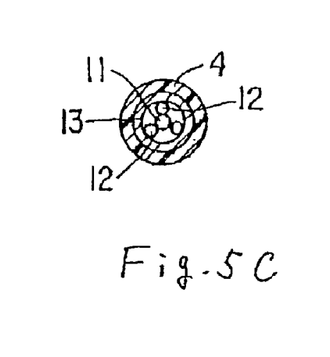
FIG. 5C illustrates a transverse sectional view taken along the line 5C-5C in FIG. 5A.

With reference to FIGS. 5A and 5B, a second embodiment of medical retrieval instrument according to the present invention will now be explained.

The medical retrieval instrument 1 according to the second embodiment has a construction in which an end portion of each holding filament 7 forming a holding section 6 is fixed to the end of the sheath 4. In this construction, the second embodiment is different from the first embodiment. In other constructions, both are the same.

The following explanation relates to the construction in which the filament is mounted according to the second embodiment. A fixing member 21 being a pipe is fixedly engaged with the outer surface of the sheath 4. The inner surface of the fixing member 21 comprises a groove 22 into which one end portion of the holding filament 7 is engaged. The groove 22 is parallel to the axial direction of the insertion section. An end portion of the holding filament 7 is engaged into the groove 22 and fixed by an adhesive. The groove 22 is covered with the sheath 4.

In the second embodiment, the end portion of the holding filament 7 forming the holding section 6 is engaged into the corresponding groove 22 of the fixing member 21. In other words, the end portion of the holding filament 7 is positioned and fixed by the groove 22. As a result, the extending direction of the holding filament 7 is correctly regulated. The assembly is also improved.

Figure 6A:
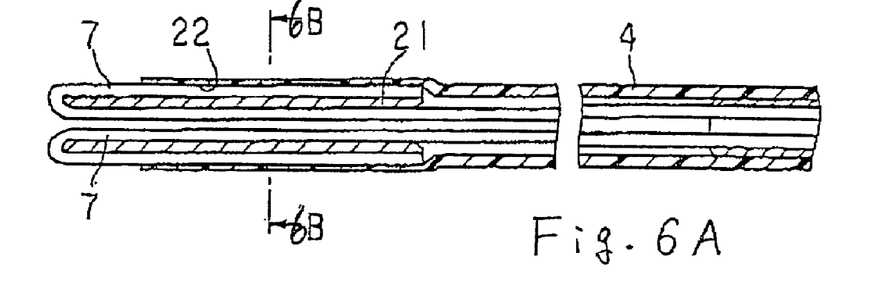
FIG. 6A illustrates a vertical section illustrating the vicinity of the distal end portion of an insertion section in a medical retrieval instrument according to a third embodiment of the present invention.
Figure 6B:
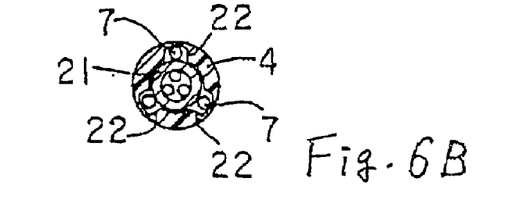
FIG. 6B illustrates a transverse sectional view taken along the line 6B-6B in FIG. 6A.

With reference to FIGS. 6A and 6B, a medical retrieval instrument according to a third embodiment of the present invention will now be explained.

The end portion of each holding filament 7 forming a holding section 6 is fixed to the distal end of a sheath 4, in a medical retrieval instrument 1 according to the third embodiment. In this constitution, the third embodiment is different from the first embodiment. In the other constitutions, both are the same.

In the third embodiment, a fixing member 21 is engaged and fixed inside the sheath 4. A groove 22 into which the end portion of the holding filament 7 is engaged is formed on an inner wall surface of the sheath 4. The groove 22 is parallel to the axial direction of the insertion section. The outer surface of the fixing member 21 covers the groove 22. Since the fixing member 21 does not comprise the groove 22, the fixing member 21 can be formed of a thin pipe member.

Figure 7A:
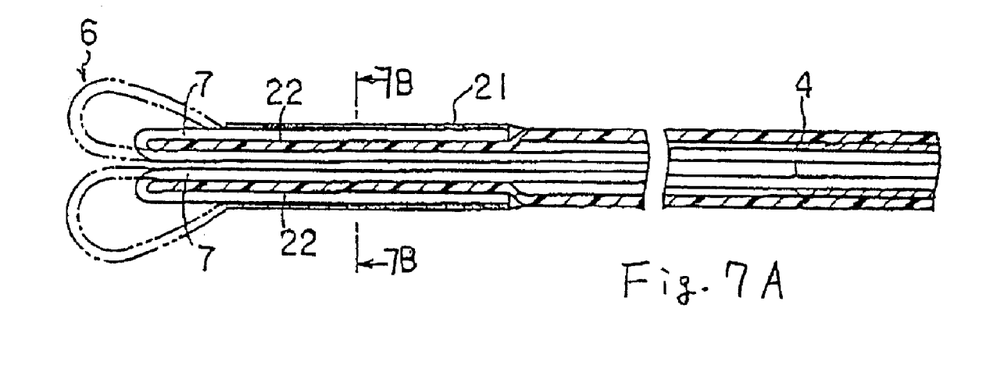
FIG. 7A illustrates a vertical section illustrating the vicinity of the distal end portion of an insertion section in a medical retrieval instrument according to a fourth embodiment of the present invention.
Figure 7B:
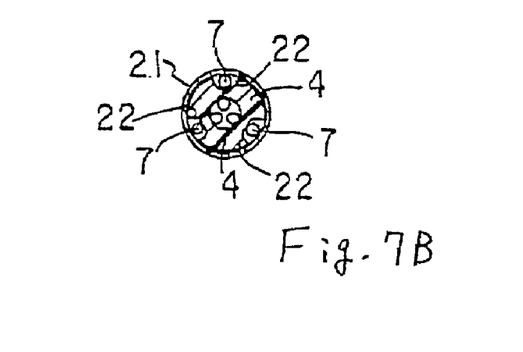
FIG. 7B illustrates a transverse sectional view taken along the line 7B-7B in FIG. 7A.

With reference to FIGS. 7A and 7B, a medical retrieval instrument according to a fourth embodiment of the present invention will now be explained.

An end portion of each holding filament 7 is fixed to the distal end of a sheath 4, in a medical retrieval instrument 1 according to the fourth embodiment. In this constitution, the fourth embodiment is different from the first embodiment. In the other constitutions, both are the same.

In this embodiment, a fixing member 21 is engaged with and fixed to the outer surface of the sheath 4. A groove 22 into which one end portion of the holding filament 7 is engaged is formed on the outer wall surface of the sheath 4. The groove 22 is parallel to the axial direction of the insertion section. The inner surface of the fixing member 21 covers the groove 22. Since the fixing member 21 does not comprise the groove 22, the fixing member 21 can be formed of a thin pipe member.

Figure 8A:
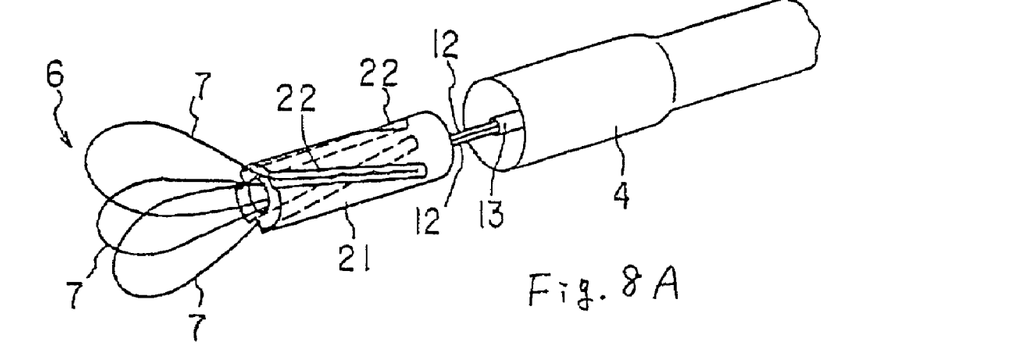
FIG. 8A illustrates an expanded perspective view showing the vicinity of the distal end portion of an insertion section in a medical retrieval instrument according to a fifth embodiment of the present invention.
Figure 8B:
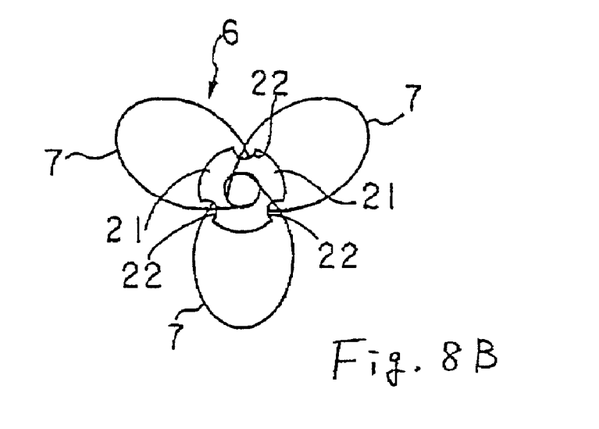
FIG. 8B illustrates a front view of a basket portion of a medical retrieval instrument according to a fifth embodiment of the present invention.

With reference to FIGS. 8A and 8B, a medical retrieval instrument according to a fifth embodiment of the present invention will now be explained.

In a medical retrieval instrument 1 according to this embodiment a groove 22 into which an end portion of each holding filament 7 forming a holding section 6 is engaged with and fixed to is slanted with respect to the axial direction of insertion the section. The slanted grooves 22 are spirally formed on the outer surface of the fixing member 21. In the other constitutions, the fifth embodiment is the same as the first embodiment. In this embodiment, the loops open outward.

Although the groove 22 is formed on the outer surface of the fixing member 21 in this embodiment, the same effect can be obtained, even if the groove 22 is formed in the sheath 4. In other words, it is also effective to provide the groove 22 being slant with respect to the axial direction of the insertion section extending outward, in the above-mentioned four embodiments.

With respect to the extending direction of the above-mentioned groove 22, the extending direction of the insertion section can be changed with the extending direction of the fixing member 21 or that of the sheath 4.

Figure 9:
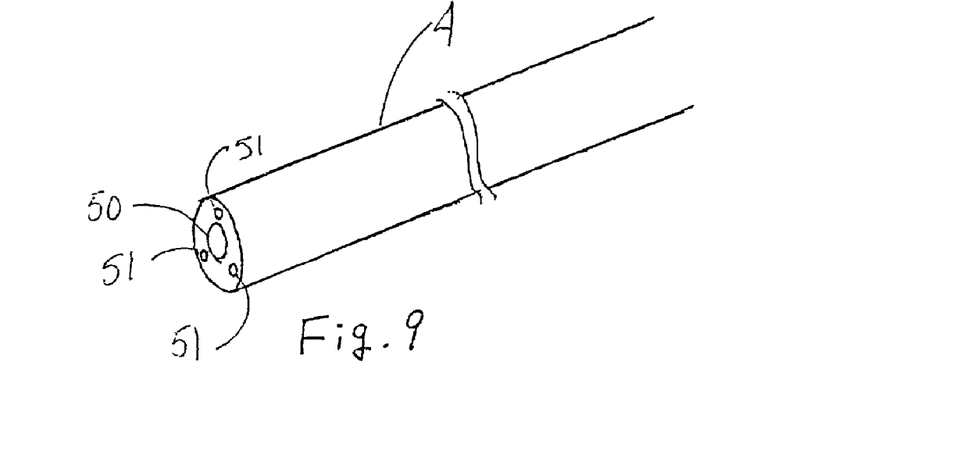
FIG. 9 illustrates a front view of an alternative distal portion of an embodiment of a medical retrieval instrument of the present invention.

The present invention is not limited to the above-mentioned embodiments. The sheath comprises the positioning and regulating groove at which an end portion of each holding filament forming the basket portion is fixed. However, such positioning and regulating groove can be formed in a member provided to the distal end of the operation wire. This constitution leads the other end of filament to be positioned, regulated and mounted. Also, a hole can be formed, instead of the positioning and regulating means by which one end portion of the filament is connected, as shown in FIG. 9. In such a configuration, the sheath 4 and the fixing member 21 can be integrally formed. With respect to a plurality of holding filaments 7 of FIG. 9, an end portion of each holding filament 7 is inserted through a central hole 50 and connected to the operation wire 5. The other end of each holding filament 7 is fixed to each of a plurality of holes 51 which are equally formed in the circumferential direction of the central hole 50 provided at the distal end of the sheath 4. This constitution also leads to the same operation and effect as the above-mentioned embodiments. This constitution advantageously needs fewer components for the distal end of the sheath 4, also. Additionally, the desired operation and effect can be advantageously obtained, only if the holding filament 7 is fixed to the hole 51.

Moreover, while one end portion of the holding filament 7 is connected to the distal end of the operation wire 5, the other end of the holding filament 7 may be led outward the sheath 4, via a through hole (not shown) formed in the fixing member 21 which is engaged in the distal end portion of the sheath 4. The other end portion of filament is then connected to the distal end of the operation wire. In this case, the above-mentioned fixing member may comprise a positioning and regulating groove, so that the other end of the operation wire is connected. The number of holding filament can be one, two, four or more. The loop shape of the holding filaments can be changed according to the use.

As mentioned above, the present invention enables the filament forming the holding section to be easily mounted at a predetermined position and in a predetermined direction.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A medical retrieval instrument comprising:
   a plurality of filaments for holding an object;
   a hollow section, through which a first end of each of the plurality of filaments passes, the hollow section including a fixing section for fixing a second end of each of the plurality of filaments;
   wherein the hollow section comprises a first member through which one end of each of the plurality of filaments passes, the hollow section comprises a second member engaged with the first member, the fixing section includes a plurality of grooves formed on an engagement surface at which the first member and the second member engage, and an elongated direction of the plurality of grooves is slanted with respect to an extending direction of the first member or an elongated direction of the second member.

2. A medical retrieval instrument comprising:
at least one filament provided in a distal end portion of the instrument for holding an object; and
a fixing member provided in the distal end portion of the instrument for at least fixing one end of the at least one filament to the instrument, the fixing member having an accommodation part for accommodating and fixing the one end of the at least one filament in a predetermined position and direction,
wherein the accommodation part is slanted in respect to the longitudinal direction of the instrument.

3. A medical retrieval instrument comprising:
a sheath;
at least one filament provided in a distal end portion of the sheath for holding an object;
a fixing member provided in the distal end portion of the sheath for fixing one end of the at least one filament to the instrument;
wherein at least one of the sheath and the fixing member has a groove for accommodating the one end of the at least one filament on its surface, the groove having an elongated shape along the direction of the at least one filament and in which the at least one filament fits, the groove being provided in a predetermined position and direction for accommodating and fixing the one end of the at least one filament in the predetermined position and direction regulated by the groove.

4. The medical retrieval instrument according to claim 3, wherein an adhesive is applied in the groove for fixing the at least one filament to the instrument.

5. A medical retrieval instrument comprising:
a sheath;
at least one filament provided in a distal end portion of the sheath for holding an object;
a fixing member provided in the distal end portion of the sheath for fixing one end of the at least one filament to the instrument;
wherein at least one of the sheath and the fixing member has a hole for accommodating the one end of the at least one filament, the hole having an elongated shape along the direction of the at least one filament and in which the at least one filament fits, and the groove being provided in a predetermined position and direction for accommodating and fixing the one end of the at least one filament in the predetermined position and direction regulated by the hole.

6. The medical retrieval instrument according to claim 5, wherein an adhesive is applied in the hole for fixing the at least one filament to the instrument.

* * * * *